US009612223B2

(12) United States Patent
Tahira et al.

(10) Patent No.: US 9,612,223 B2
(45) Date of Patent: Apr. 4, 2017

(54) METHOD FOR MANUFACTURING SENSOR INTERMEDIATE PRODUCT AND METHOD FOR MANUFACTURING SENSOR

(71) Applicant: NGK SPARK PLUG CO., LTD., Nagoya-shi, Aichi-ken (JP)

(72) Inventors: Daisuke Tahira, Komaki (JP); Keiichi Noda, Ichinomiya (JP); Shingo Ito, Ichinomiya (JP); Atsunori Okada, Komaki (JP); Yuichi Yamada, Komaki (JP)

(73) Assignee: NGK SPARK PLUG CO., LTD., Nagoya (JP)

( * ) Notice: Subject to any disclaimer, the term of this patent is extended or adjusted under 35 U.S.C. 154(b) by 30 days.

(21) Appl. No.: 14/710,762

(22) Filed: May 13, 2015

(65) Prior Publication Data
US 2015/0330939 A1    Nov. 19, 2015

(30) Foreign Application Priority Data

May 13, 2014 (JP) ................................ 2014-099529
Feb. 12, 2015 (JP) ................................ 2015-025007

(51) Int. Cl.
*G01N 27/407* (2006.01)
*G01N 27/409* (2006.01)

(52) U.S. Cl.
CPC ....... *G01N 27/4077* (2013.01); *G01N 27/409* (2013.01); *G01N 27/4078* (2013.01); *Y10T 29/42* (2015.01); *Y10T 29/49904* (2015.01); *Y10T 29/49908* (2015.01)

(58) Field of Classification Search
CPC .......... G01N 27/4077; G01N 27/4078; G01N 27/409; Y10T 29/49908; Y10T 29/42; Y10T 29/49904
See application file for complete search history.

(56) References Cited

U.S. PATENT DOCUMENTS 9,354,142 B2 * 5/2016 Tahira ................. G01M 15/102

FOREIGN PATENT DOCUMENTS

JP    2008-145339 A    6/2008
JP    2012-242112 A    12/2012

* cited by examiner

*Primary Examiner* — John C Hong
(74) *Attorney, Agent, or Firm* — Stites & Harbison, PLLC; Jeffrey A. Haeberlin; James R. Hayne

(57) ABSTRACT

A method for manufacturing a sensor intermediate product includes: disposing a tubular holder and a tubular compact in a tubular metallic shell, and inserting a metallic pin into a first insertion hole of the holder and a second insertion hole of the compact; compressing the compact so as to form a filling member intermediate having a shape which brings the filling member intermediate into pressure contact with the inner wall surface of the metallic shell and allows removal of the metallic pin from the second insertion hole; pulling out the metallic pin from the first insertion hole and the second insertion hole; inserting a sensor element into the first insertion hole and the second insertion hole; and compressing the filling member intermediate to thereby form a filling member which fixes the sensor element inside of the metallic shell.

7 Claims, 6 Drawing Sheets

METHOD FOR MANUFACTURING SENSOR INTERMEDIATE PRODUCT AND METHOD FOR MANUFACTURING SENSOR

CROSS REFERENCE TO RELATED APPLICATIONS

The present application claims priority from Japanese Patent Application No. 2014-099529, filed on May 13, 2014, and Japanese Patent Application No. 2015-025007, filed on Feb. 12, 2015, the disclosures of which are herein incorporated by reference in their entirety.

BACKGROUND OF THE INVENTION

Field of the Invention

The present invention relates to a method for manufacturing a sensor intermediate product having a sensor element for detecting the concentration of a gas to be detected, and to a method for manufacturing a sensor using the sensor intermediate product.

Description of Related Art

A known gas sensor for detecting the concentration of oxygen or NOx contained in exhaust gas discharged from an automobile or the like has a sensor element including a solid electrolyte member.

Such a gas sensor is known to have a structure in which a sensor element is inserted into a tubular metallic shell (housing) to be fixed to an exhaust pipe and is held such that its one end is exposed to a gas to be measured. In order to stably hold the sensor element inside the metallic shell and prevent entry of exhaust gas into the interior of the gas sensor, a holder for holding the sensor element, talc powder (filling member), a press member for pressing and compressing the talc powder, etc. are stacked, in this order from the forward end, within a space between the inner circumferential surface of the metallic shell and the outer circumferential surface of the sensor element. The sensor element is fixed inside the metallic shell as a result of the talc powder being compressed such that the talc powder is charged in the space between the metallic shell and the sensor element under pressure.

Incidentally, as shown in FIG. 5, compression of talc powder is performed as follows in a conventional gas sensor manufacturing method (see Patent Documents 1 and 2). First, a ceramic ring 300 and a second talc ring 226 are accommodated in a metal cup 20 with a sensor element 21 inserted therethrough (second disposing step), and the second talc ring 226 is compressed from the opening side of the metal cup 20 (second compression step). As a result, the second talc ring 226 is crushed and becomes powdery second talc 220, whereby an element unit 230 in which the sensor element 21 is held within the metal cup 20 and is united therewith is formed.

Next, the element unit 230 is inserted into a metallic shell 11 from the rear end side (the side toward a cylindrical portion for crimping 16) of a shell assembly 235, and a first talc ring 225, a sleeve 43, and a ring washer 45 are fitted onto the sensor element 21 from the side where the rear end 29 of the sensor element 21 is present (holding step). Subsequently, while the first talc ring 225 is being compressed, the cylindrical portion for crimping 16 is bent radially inward by means of heat crimping (first compression step), whereby a gas sensor is assembled.

Notably, in some cases, after the above-described first compression step, a protection sleeve (not shown) is fixed to the rear end of the metallic shell 11 by means of welding or the like, whereby a gas sensor is manufactured. Also, in some cases, after the sensor intermediate product having undergone the first compression step is made, this sensor intermediate product is transferred to a location for a different step, and the protection sleeve is then attached thereto so as to manufacture the gas sensor. Namely, the manufacturing process is divided into an intermediate step of manufacturing a sensor intermediate product and an assembly step of assembling the gas sensor for manufacture of the gas sensor.

RELATED ART DOCUMENTS

Patent Document 1 is Japanese Patent Application Laid-Open (kokai) No. 2012-242112 (FIG. 5).
Patent Document 2 is Japanese Patent Application Laid-Open (kokai) No. 2008-145339 (FIG. 4).

BRIEF SUMMARY OF THE INVENTION

As described above, in the conventional gas sensor manufacturing process, the second talc ring 226 is compressed within the metal cup 20 (second compression step), and the first talc ring 225 is first compressed within the metallic shell 11 (first compression step). In this case, when the second talc ring 226 is first compressed within the metal cup 20, the element unit 230 may be formed in a state in which the axis of the sensor element 21 and the axis of the element unit 230 deviate from each other. If this element unit 230 is inserted into the metallic shell 11, there is created a state in which the axis of the sensor element 21 and the axis of the metallic shell 11 deviate from each other. If the first talc ring 225 is inserted into the metallic shell 11 in such a state, and the first talc ring 225 is compressed, the first talc ring 225 flows such that the axis of the sensor element 21 is aligned with the axis of the metallic shell 11. As a result, a shearing stress acts on the sensor element 21 and the sensor element 21 may break.

A conceivable way of solving such a problem is abolishing the element unit, fitting a single talc ring onto the sensor element 21 without using the metal cup 20, and compressing the talc ring within the metallic shell 11 in a single operation.

However, even in the case where the talc ring is compressed within the metallic shell 11 in a single operation, when the talc ring is compressed and the resultant talc powder flows (relocates), the talc powder flows such that the talc powder is distributed substantially uniformly within the metallic shell. Therefore, if a portion of the talc ring has a shape-related defect caused by, for example, chipping of the talc ring, the stress acting on the sensor element 21 through the wall surface of the insertion hole of the talc ring becomes non-uniform, and a shearing stress acts on the sensor element 21, which may result in breakage of the element.

In view of the foregoing, an object of the present invention is to provide a method for manufacturing a sensor intermediate product which prevents breakage of a sensor element, which breakage would otherwise occur when a filling member for fixing the sensor element inside a metallic shell is disposed in the metallic shell. Another object of the present invention is to provide a method for manufacturing a sensor.

According to one aspect of the invention, a method for manufacturing a sensor intermediate product includes a preparation step of preparing a preliminary assembly in which a tubular holder and a tubular compact are disposed in a tubular metallic shell, the tubular compact being formed by compacting powder of a filling member, the tubular metallic shell defining (i.e., having) a through hole, having an inner wall surface with a circumference, and including a step portion projecting inward along the circumference of the inner wall surface of the metallic shell in such a manner that the holder is engaged with the step portion and the compact is stacked on a side of the holder opposite the step portion, and a metallic pin is inserted into a first insertion hole of the holder and a second insertion hole of the compact. The method further includes a pre-compression step of compressing the compact so as to form a filling member intermediate having a shape which brings the filling member intermediate into pressure contact with the inner wall surface of the metallic shell and allows removal of the metallic pin from the second insertion hole; a pin pulling out step of pulling out the metallic pin from the first insertion hole and the second insertion hole; an insertion step of inserting an axially extending sensor element into the first insertion hole and the second insertion hole; and a main compression step of compressing the filling member intermediate to thereby form the filling member which fixes the sensor element inside of the metallic shell.

According to this method for manufacturing a sensor intermediate product, as a result of the pre-compression step, the powder which constitutes the compact is caused to flow (relocate) around the metallic pin, and is solidified in a state in which it is in pressure contact with the inner wall surface of the metallic shell, whereby the filling member intermediate is formed. At that time, if a portion of the compact has a shape-related defect caused by chipping or the like, the stress acting on the metallic pin may become non-uniform when the powder flows (relocates) around the metallic pin as a result of the pre-compression step. However, even in such a case, the metallic pin neither breaks nor deforms, because the metallic pin is formed of metal.

In addition, since the filling member intermediate formed by the pre-compression step is such that the powder constituting the filling member intermediate is disposed approximately uniformly, occurrence of a shape-related defect can be restrained. Accordingly, when the powder constituting the filling member intermediate flows (relocates) around the sensor element as a result of the subsequent main compression step to thereby form the filling member, it is possible to prevent non-uniform stress from acting on the sensor element through the wall surface of the second insertion hole, to thereby prevent breakage of the sensor element.

Further, the filling member intermediate formed by the pre-compression step has a shape which brings the filling member intermediate into pressure contact with the inner wall surface of the metallic shell and allows removal of the metallic pin from the second insertion hole. Therefore, even when the metallic pin is pulled out in the subsequent pin pulling out step, the filling member intermediate neither collapses nor comes off the metallic shell. Therefore, the shape of the filling member intermediate including the second insertion hole can be maintained. Further, when the sensor element is inserted into the second insertion hole in the insertion step, no stress acts on the sensor element. Therefore, the sensor element can be easily inserted into the filling member intermediate.

In an embodiment of the method for manufacturing a sensor intermediate product, the sensor element may have a detection section provided on a forward end side of the sensor element and adapted to detect a specific gas component contained in a gas to be detected, and a protection layer provided on the forward end side of the sensor element and covering the detection section; and, in the insertion step, a portion of the sensor element located on the rear end side may be inserted into the first insertion hole and the second insertion hole from a forward end side of the metallic shell.

According to this method for manufacturing a sensor intermediate product, even in the case where a portion of the sensor element located on the forward end side is covered with a protection layer which is larger in transverse cross section than the sensor element itself, the sensor element can be inserted into the first insertion hole and the second insertion hole from the rear end side of the sensor element, and the manufacturing method of the present invention can be applied.

The method for manufacturing a sensor intermediate product may be such that, in the pin pulling out step, an axial position to which the metallic pin is pulled out is adjusted such that a forward end of the metallic pin will come into contact with a forward end or a rear end of the sensor element inserted in the insertion step; and, in the insertion step, the forward end or the rear end of the sensor element is brought into contact with the forward end of the metallic pin.

According to this method for manufacturing a sensor intermediate product, the forward end of the metallic pin whose pull-out position has been adjusted within the support hole comes into contact with the forward end or rear end of the sensor element. Therefore, the insertion depth of the sensor element in the axial direction; i.e., the position at which the sensor element is fixed to the metallic shell, can be defined by the metallic pin, whereby positioning of the sensor element is facilitated.

The sensor may have the shape of a plate having a rectangular cross section and extending in a longitudinal direction.

When the sensor element has a plate-like shape, the axis of the sensor element and the axis of the element unit are likely to deviate from each other. Therefore, the present invention becomes particularly effective.

According to another aspect of the invention, a sensor includes a plate-shaped sensor element extending in a direction of an axis, a tubular metallic shell surrounding the sensor element in such a manner that a forward end of the sensor element projects from the metallic shell, a holder and a filling member disposed between the metallic shell and the sensor element, and a protection sleeve fixed to a rear end portion of the metallic shell. A method of manufacturing the sensor includes a sensor intermediate product forming step of forming the above-described sensor intermediate product; and an assembly step of fixing the protection sleeve to the rear end portion of the metallic shell after the sensor intermediate product forming step.

The present invention is also effective in the case where the sensor intermediate product forming step and the assembly step (sensor manufacturing step) are performed separately.

The present invention can prevent breakage of the sensor element, which breakage would otherwise occur when the filling member for fixing the sensor element inside the metallic shell is disposed in the metallic shell.

BRIEF DESCRIPTION OF THE DRAWINGS

Illustrative aspects of the invention will be described in detail with reference to the following figures wherein.

DETAILED DESCRIPTION OF EXEMPLARY EMBODIMENTS OF THE INVENTION

Figure 3:
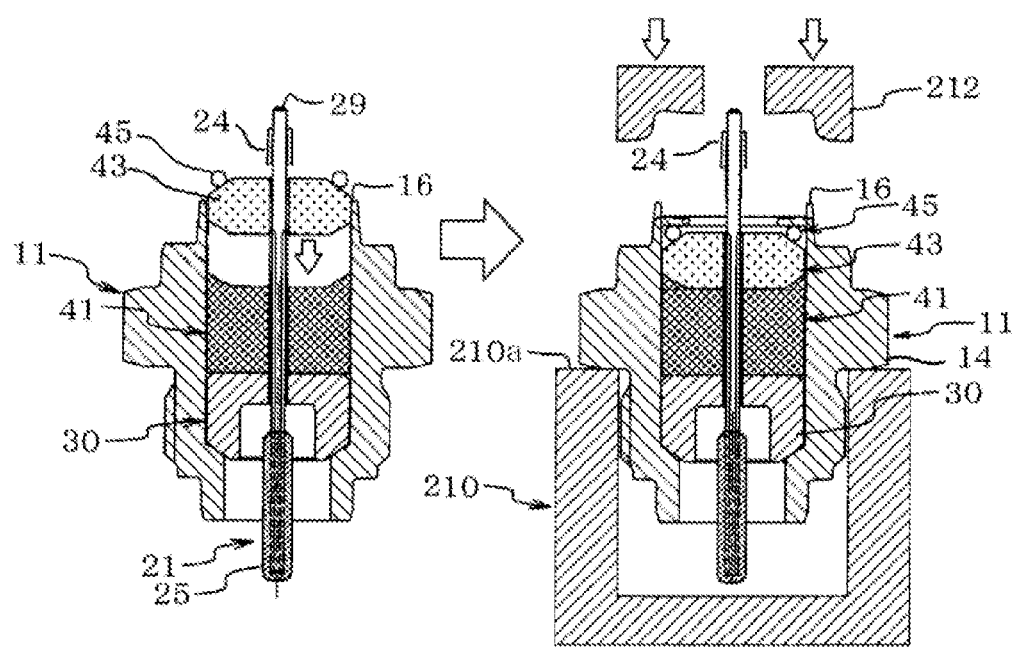
FIG. 3 is a view showing a step subsequent to the steps of the method for manufacturing a gas sensor intermediate product according to the embodiment of the present invention.
Figure 4:
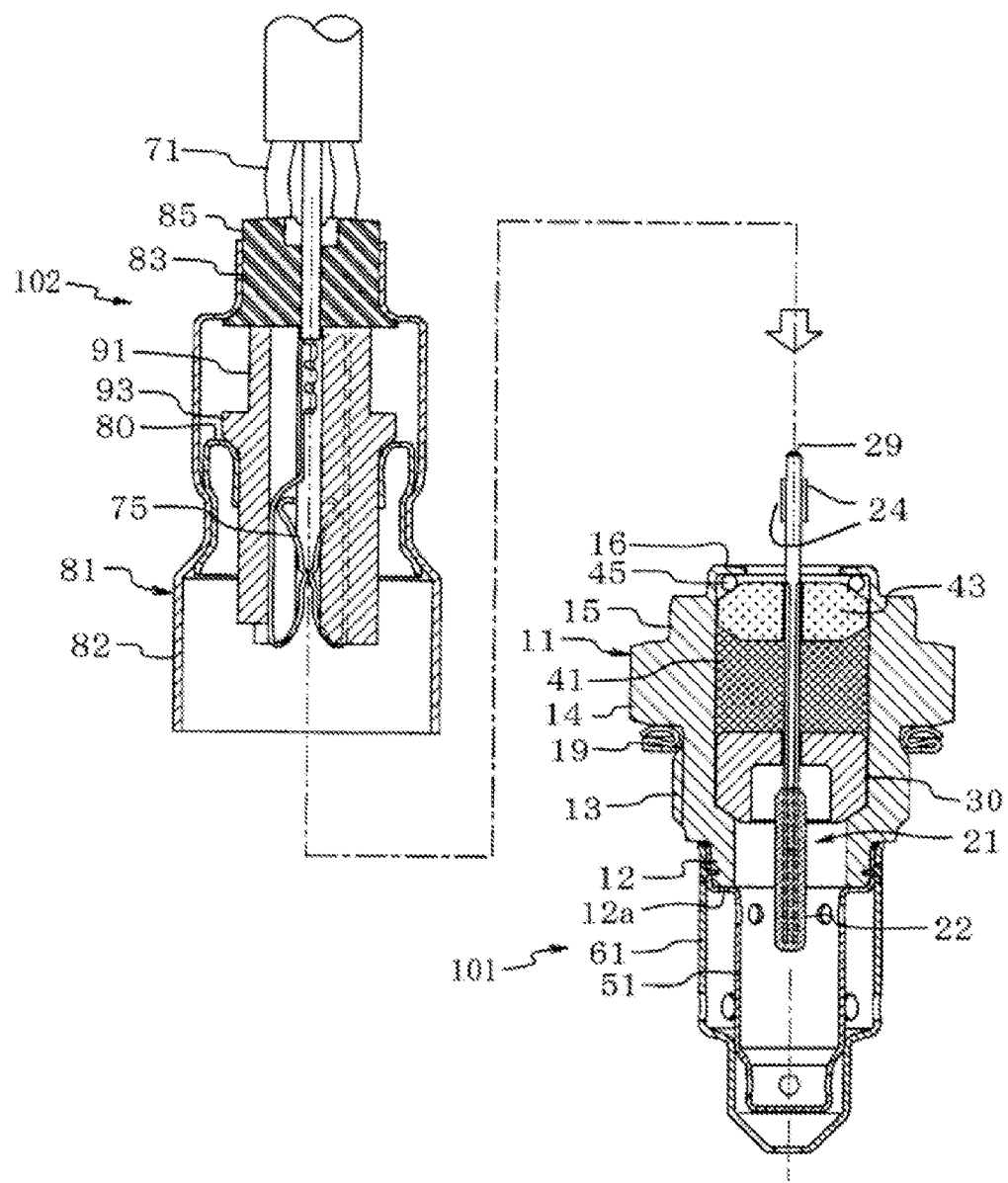
FIG. 4 is a view showing the final step of the manufacture and assembly of the gas sensor.
Figure 5:
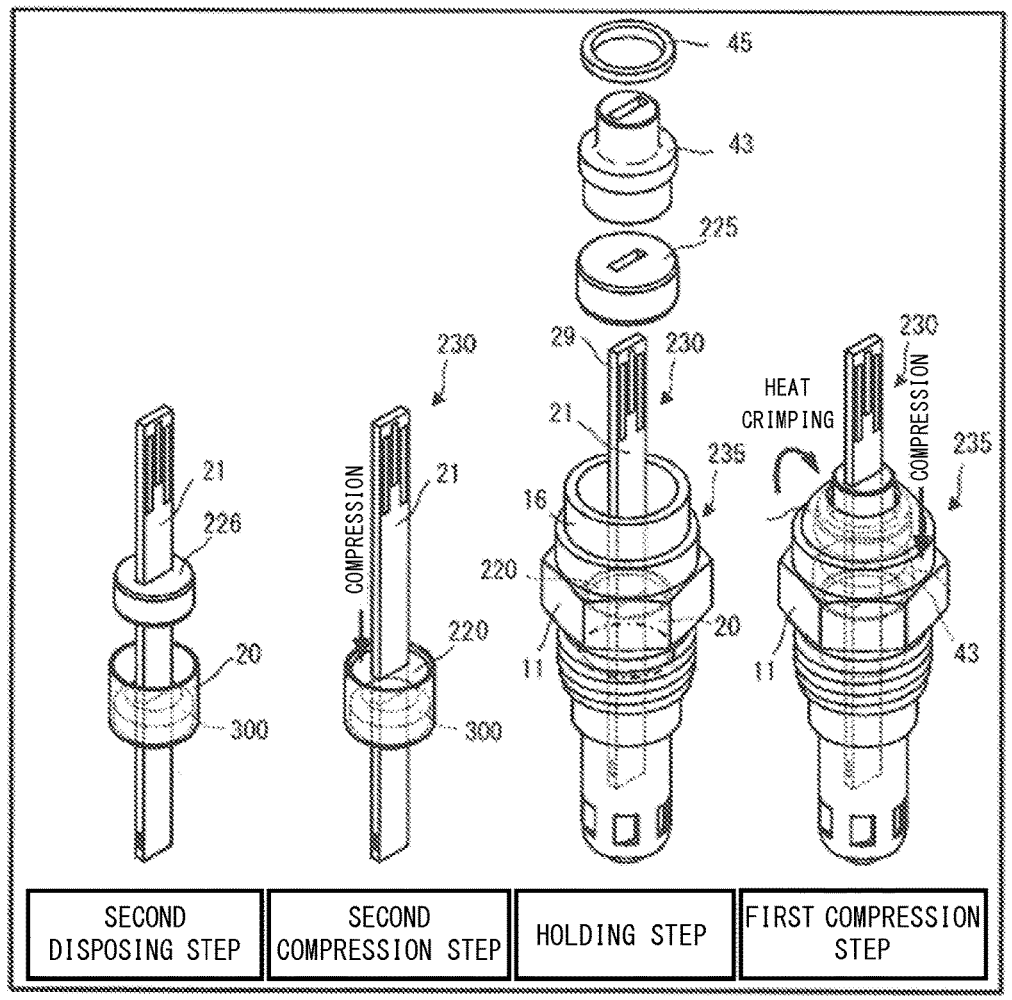
FIG. 5 is an illustration showing the steps of a conventional method for manufacturing a gas sensor.

An embodiment of the present invention will now be described. In the following description, a term "method for manufacturing a sensor intermediate product" and a term "method for manufacturing a sensor" will be used when necessary. Steps up to a main compression step correspond to the "method for manufacturing a sensor intermediate product," and all the steps, including an assembly step of fixing a protection sleeve 81 (see FIG. 4) to the sensor intermediate product after the main compression step, correspond to the "method for manufacturing a sensor." For example, in the present embodiment, after a sensor intermediate product is manufactured by the steps shown in FIGS. 2(a) through 2(g), the protection sleeve 81 (semi-assembly 102) is fixed to a rear end portion of a metallic shell 11, whereby a gas sensor 1 is manufactured as shown in FIGS. 3 and 4. Accordingly, the steps shown in FIGS. 2(a) through 2(g) correspond to the "method for manufacturing a sensor intermediate product," and the steps shown in FIGS. 2(a)-2(g), 3, and 4 corresponds to the "method for manufacturing a sensor." Also, the step shown in FIG. 4 corresponds to the "assembly step."

Figure 1:
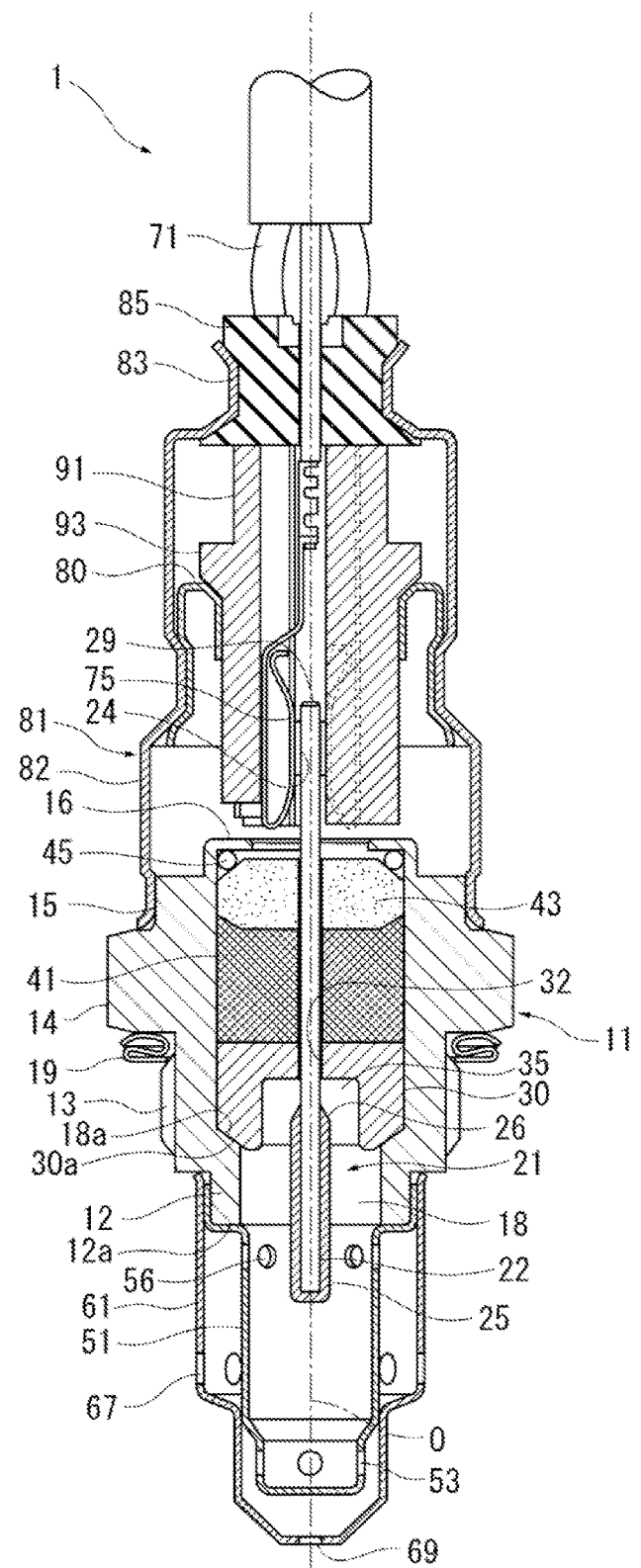
FIG. 1 is a sectional view of a gas sensor (full-range air fuel ratio gas sensor) manufactured by an embodiment of the present invention, the view being taken along a longitudinal direction of the gas sensor.

FIG. 1 is a sectional view of the gas sensor (full-range air fuel ratio gas sensor) 1 manufactured by the embodiment of the present invention, the view being taken along a longitudinal direction (the direction of the axis O) thereof. FIGS. 2(a) through 2(g) are views showing the steps of the method for manufacturing a sensor intermediate product according to the embodiment of the present invention.

As shown in FIG. 1, the gas sensor (full-range air fuel ratio gas sensor) 1 includes a sensor element 21; a ceramic holder 30 having a first insertion hole 32 in which the sensor element 21 is inserted; and the metallic shell 11 which surrounds the radially outer circumference of the ceramic holder 30. The ceramic holder 30 corresponds to the "holder" in the claims.

A portion of the sensor element 21 which is located near the forward end thereof and on which a detection section 22 to be described later is formed projects forward from a forward-facing surface 30a of the ceramic holder 30. By means of compressing a filling member (talc in the present example) 41 disposed on a rear end surface side (the upper side in FIG. 1) of the ceramic holder 30 in the forward-rear direction via a sleeve 43 formed of an insulating material and a ring washer 45, the sensor element 21 inserted into the first insertion hole 32 is fixed within the metallic shell 11 in a state in which airtightness is secured in the forward-rear direction. Notably, a portion of the sensor element 21 which is located on the side toward the rear end 29 thereof and includes the rear end 29 projects rearward from the sleeve 43 and the metallic shell 11, and metallic terminals 75 provided at the ends of lead wires 71 extending outward through a seal member (e.g., a grommet formed of rubber) 85 are in pressure-contact with and are electrically connected to electrode terminals 24 formed on the portion near the rear end 29. Also, the portion of the sensor element 21 which is located near the rear end 29 and includes the electrode terminals 24 is covered with the protection sleeve 81. The gas sensor 1 will be described in more detail below.

The sensor element 21, which has a strip-like (plate-like) shape, extends in the direction of the axis O, and has a detection section 22 which is formed on a forward end portion thereof (on the lower side in FIG. 1) exposed to a measurement target (gas to be detected). The detection section 22 is composed of electrodes for detection, etc. (not shown), and is adapted to detect a specific gas component contained in the gas to be detected. The sensor element 21 has a rectangular transverse cross section whose size is constant along the forward-rear direction, and is formed mainly of ceramic (solid electrolyte or the like) to have an elongated shape. The detection section 22 of the sensor element 21 is covered with a porous protection layer 25 formed of alumina, spinel, or the like. This protection layer 25 has a water resistance and a poisoning resistance. In a region where the protection layer 25 is formed, the size of the transverse cross section increases by an amount corresponding to the thickness of the protection layer 25 (e.g., 0.5 to 0.6 mm) (the thickness is exaggerated in the drawing). The sensor element 21 itself is the same as a conventionally known sensor element. A pair of electrodes for detection which constitute the detection section 22 are disposed on a portion of a solid electrolyte (member) near the forward end thereof, and electrode terminals 24 communicating with the electrodes for detection are formed, in an exposed state, on a portion of the solid electrolyte (member) near the rear end thereof. Lead wires 71 for taking out an output to be detected are connected to the electrode terminals 24. Also, in the present examples, a heater (not shown) is provided in a portion of a ceramic member which is layered on the solid electrolyte (member) of the sensor element 21, the portion being located near the forward end of the ceramic member. Electrode terminals 24 to which lead wires 71 for applying a voltage to the heater are connected are formed, in an exposed state, on a portion of the ceramic member located near the rear end thereof. Notably, although not illustrated, these electrode terminals 24 are formed into a vertically elongated rectangular shape, and are disposed near the rear end 29 of the sensor element 21 in such a manner that three or two electrode terminals are laterally juxtaposed on each of wide surfaces (opposite surfaces) of the strip-like sensor element.

The metallic shell 11 has the shape of a tube having portions which are coaxial in the forward-rear direction and have different diameters. The metallic shell 11 has, on its forward end side, a cylindrical tubular annular portion (hereinafter also referred to as the "cylindrical portion") 12, which is small in diameter and onto which protectors 51 and 61 (which will be described later), are fitted and fixed. A screw 13 which is larger in diameter than the cylindrical portion 12 and is used to fix the gas sensor 1 to the exhaust pipe of an engine is proved on the outer circumferential surface located rearward (upward in the drawing) of the cylindrical portion 12. A polygonal portion 14 for screwing the sensor 1 by using the screw 13 is provided rearward of the screw 13. Also, a cylindrical portion 15 is provided rearward of the polygonal portion 14 to be located adjacent thereto. The protection sleeve (outer sleeve) 81 for covering a rear portion of the gas sensor 1 is fitted onto the cylindrical portion 15, and is welded thereto. A cylindrical portion for crimping 16, which is smaller in outer diameter than the cylindrical portion 15 and has a small wall thickness, is provided rearward of the cylindrical portion 15. Notably, since FIG. 1 shows the state after crimping, the cylindrical portion for crimping 16 is bent inward. Notably, a gasket 19 for establishing a seal when the sensor 1 is screwed is attached to the lower surface of the polygonal portion 14.

Also, the metallic shell 11 has an inner hole (through hole) 18 extending therethrough in the direction of the axis O. The diameter of the inner hole 18 increases from the diameter at the forward end thereof to the diameter at the rear end thereof, at a step portion 18a which is tapered such that its diameter decreases toward the forward end.

A ceramic holder 30 formed of an insulating ceramic (e.g., alumina) and generally having the shape of a short cylinder is disposed inside the metallic shell 11. The ceramic holder 30 is tapered such that its diameter decreases toward the forward end thereof, and a taper surface on the outer periphery side thereof forms a forward-facing surface 30a. The ceramic holder 30 is positioned within the metallic shell 11, as a result of engagement of the forward-facing surface 30a with the step portion 18a, with a gap formed between the ceramic holder 30 and the metallic shell 11.

Meanwhile, the first insertion hole 32 is provided at the center of the ceramic holder 30, and forms a rectangular opening having approximately the same dimensions as those of the transverse cross section of the sensor element 21 so that a portion of the sensor element 21 located rearward of the protection layer 25 passes through the first insertion hole 32 with substantially no gap formed.

A circular recess 35 which is larger in diameter than the first insertion hole 32 is formed on the forward end side of the first insertion hole 32. The recess 35 extends rearward from the forward-facing surface 30a of the ceramic holder 30 and communicates with the forward end of the first insertion hole 32. The bottom surface of the recess 35 (at the position of the forward end of the insertion hole 32) is flat.

The sensor element 21 is inserted into the first insertion hole 32 in such a manner that the forward end of the sensor element 21 projects forward from the forward-facing surface 30a of the ceramic holder 30 and the forward end 12a of the metallic shell 11. A rear end portion 26 of the protection layer 25 is accommodated in the recess 35. Notably, in order to prevent the protection layer 25 from colliding with a portion around the insertion hole 32 and being damaged when the sensor element 21 is inserted into the first insertion hole 32 of the ceramic holder 30 for assembly, it is preferred to separate the rear end portion 26 of the protection layer 25 forward from the forward end of the first insertion hole 32 (the bottom surface of the recess 35). The axial length of the rear end portion 26 of the protection layer 25 accommodated within the recess 35 is rendered smaller than the axial length of a forward end portion thereof which is disposed outside the recess 35. This configuration suppresses deterioration of the detection accuracy of the sensor element 21.

Meanwhile, a forward end portion of the sensor element 21 is covered with a double-wall protector. In the present embodiment, the double-wall protector is composed of cylindrical tubular protectors (protection covers) 51 and 61 each having a bottom and gas passage openings (holes) 56 or 67. Of the two protectors 51 and 61, the inner protector 51 has a rear end which is fitted onto the cylindrical portion 12 of the metallic shell 11, and is welded thereto. Notably, the gas passage openings 56 are provided in a rear end portion of the protector 51, for example, at 8 locations in the circumferential direction.

Meanwhile, discharge holes 53 are provided in a forward end portion of the protector 51, for example, at 4 locations in the circumferential direction. The outer protector 61 is fitted onto the inner protector 51, and is welded to the cylindrical portion 12 at the same time. The gas passage openings 67 of the outer protector 61 are provided in a portion of the protector 61 near the forward end thereof, for example, at 8 locations in the circumferential direction. Also, a discharge hole 69 is provided at the center of a bottom portion of the protector 61 located on the forward end thereof.

The metallic terminals 75 provided at the ends of the lead wires 71 extended to the outside through the seal member 85 comes, due to their spring forces, into pressure contact with the electrode terminals 24 formed on the portion of the sensor element 21 near the rear end 29 thereof, and are electrically connected thereto. In the gas sensor 1 of the present example, the metallic terminals 75, including the pressure contact portions, are provided in corresponding accommodation spaces provided in a metallic terminal holding member 91, which is disposed in the protection sleeve (metallic sleeve) 81 and is formed of an insulating material, in such a manner that each metallic terminal 75 faces another metallic terminal 75. The protection sleeve 81 is a cylindrical tubular member having portions which differ in diameter from one another. Notably, movements of the metallic terminal holding member 91 in the radial direction and toward the forward end side are restricted by an annular support member 80 fixedly provided in the protection sleeve (metallic sleeve) 81. A forward end portion (large diameter sleeve portion) 82 of this protection sleeve 81 is fitted onto and welded to the cylindrical portion 15 of the metallic shell 11 located near the rear end thereof, whereby a rear portion of the gas sensor 1 is airtightly covered. Notably, the lead wires 71 are extended to the outside through the seal member 85 disposed inside a small diameter sleeve portion 83 of the protection sleeve 81 located at the rear end thereof. The seal member 85 is compressed as a result of a decrease in the diameter of the small diameter sleeve portion 83 caused by crimping, whereby the airtightness of that portion can be secured.

Incidentally, the seal member 85 is disposed in such a manner as to press forward the rear end of the metallic terminal holding member 91. As a result, the mounting stability of the metallic terminal holding member 91 and the metallic terminals 75 provided therein is secured. Notably, since a flange 93 formed on the outer circumference of the metallic terminal holding member 91 is supported on the annular support member 80 fixedly disposed within the protection sleeve 81, the compression force of the seal member 85 is received by the support member 80.

Next, the steps of the method for manufacturing a sensor intermediate product according to the embodiment of the present invention will be described with reference to FIGS. 2(a) through 2(g).

Figure 2A:
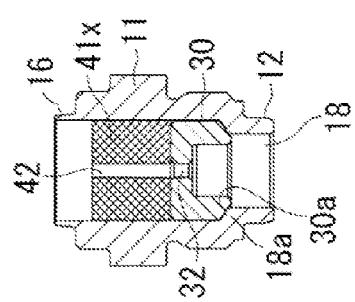
FIGS. 2(a) through 2(g) are views showing the steps of a method for manufacturing a gas sensor intermediate product according to the embodiment of the present invention.

First, as shown in FIG. 2(a), the ceramic holder 30 and a talc ring 41x (which corresponds to the "compact" in the claims) obtained by compacting the powder which constitutes the filling member 41 are disposed, in this order, in the metallic shell 11 from the forward end side in the direction of the axis O, and the forward-facing surface 30a of the ceramic holder 30 is engaged with the step portion 18a. The first insertion hole 32 of the ceramic holder 30 and a second insertion hole 42 of the talc ring 41x are aligned with each other within the metallic shell 11, and communicate with each other. Notably, the side toward the cylindrical portion 12 of the metallic shell 11 is the "forward end side" in the direction of the axis O, and the side toward the cylindrical portion for crimping 16 is the "rear end side."

The talc ring 41x is a compact which is prepared in order to facilitate handling of the powder (in the present example, talc powder) constituting the filling member. Specifically, the powder is charged into a die and is compressed, whereby a cylindrical compact having the second insertion hole 42 formed therein is produced as the talc ring 41x. When the talc ring 41x is compressed, the powder is caused to flow (relocate) and is solidified, whereby the filling member 41 in which the gaps between the particles are eliminated is obtained.

Figure 2B:
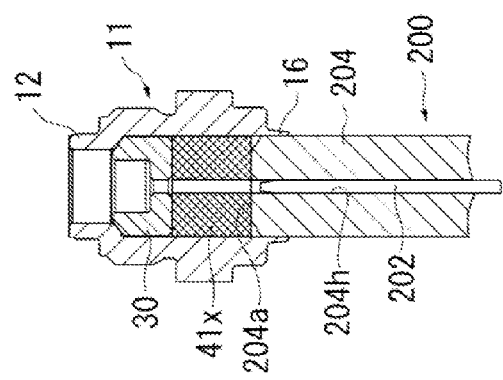

Next, as shown in FIG. 2(b), the metallic shell 11 is tuned upside down, and is fitted onto a jig 200. The jig 200 has a cylindrical tube portion 204 and a metallic pin 202 which is inserted into a center hole 204h of the tube portion 204 and vertically moves within the center hole 204h in the direction of the axis O. The outer diameter of the tube portion 204 of the jig 200 is slightly smaller than the inner diameter of the cylindrical portion for crimping 16 of the metallic shell 11.

Accordingly, when the metallic shell 11 holding the ceramic holder 30 and the talc ring 41x therein is fitted onto the tube portion 204 in such a manner that the cylindrical portion for crimping 16 is first fitted onto the tube portion 204, the metallic shell 11 is placed on the jig 200 in a state in which the talc ring 41x is in contact with a top surface 204a of the tube portion 204.

Figure 2C:
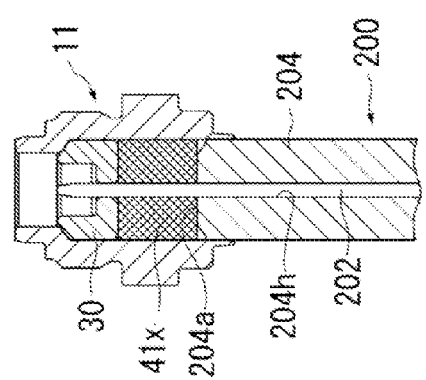

Next, as shown in FIG. 2(c), the metallic pin 202 is caused to project upward from the top surface 204a of the tube portion 204 so that the metallic pin 202 is inserted into the first insertion hole 32 and the second insertion hole 42. Notably, the transverse cross section of the metallic pin 202 has the same dimensions and shape (in the present example, a rectangular shape) as the transverse cross section of the sensor element 21. Notably, the steps shown in FIGS. 2(a) through 2(c) correspond to the "preparation step" in the claims, and the assembly shown in FIG. 2(c) corresponds to the "preliminary assembly" in the claims.

Figure 2D:
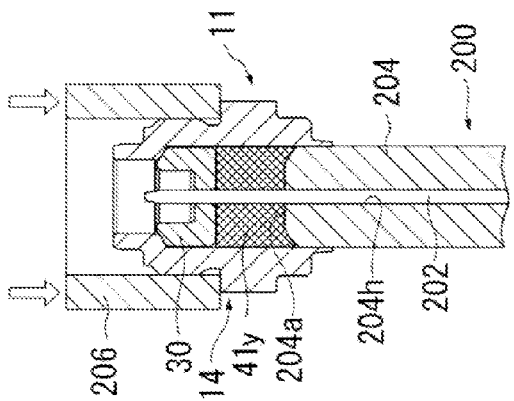

Next, as shown in FIG. 2(d), a tubular pressing jig 206 is brought into contact with the upper surface of the polygonal portion 14 of the metallic shell 11, and the pressing jig 206 is pressed downward (toward the jig 200). As a result, the talc ring 41x is compressed by the ceramic holder 30 and the jig 200. In this step, the talc ring 41x is compressed in such a manner that a filling member intermediate 41y (see FIG. 2(e)) formed as a result of the talc ring 41x being compressed has a shape which brings the filling member intermediate 41y into pressure contact with the inner wall surface of the metallic shell 11, and allows removal of the metallic pin 202 from the second insertion hole 42. Specifically, the talc ring 41x is brought into a compressed state in which the filling member intermediate 41y does not fall from the metallic shell 11 due to its weight and the filling member intermediate 41y maintains the shape even after the metallic pin 202 is pulled out. Notably, the step shown in FIG. 2(d) corresponds to the "pre-compression step" in the claims.

As a result of the pre-compression step, the powder which constitutes the talc ring 41x is caused to flow (relocate) to the circumference of the metallic pin 202, and is solidified in a state in which it is in pressure contact with the inner wall surface of the metallic shell 11, whereby the filling member intermediate 41y is formed. At that time, if a portion of the talc ring 41x has a shape-related defect caused by chipping or the like, the stress acting on the metallic pin 202 may become non-uniform when the powder flows (relocates) to the circumference of the metallic pin 202 as a result of the pre-compression step. However, even in such a case, the metallic pin 202 neither breaks nor deforms, because the metallic pin 202 is formed of metal.

Further, the filling member intermediate 41y formed by the pre-compression step has a shape which brings the filling member intermediate 41y into pressure contact with the inner wall surface of the metallic shell 11 and allows free fall of the metallic pin from the second insertion hole 42. Therefore, even when the metallic pin 202 is pulled out in a subsequent pin pulling out step, the filling member intermediate 41y neither collapses nor comes off the metallic shell 11. Therefore, the shape of the filling member intermediate 41y, including the second insertion hole 42, can be maintained. Further, when the sensor element 21 is inserted into the second insertion hole 42 in an insertion step, no stress acts on the sensor element 21. Therefore, the sensor element 21 can be easily inserted into the filling member intermediate 41y.

Figure 2E:
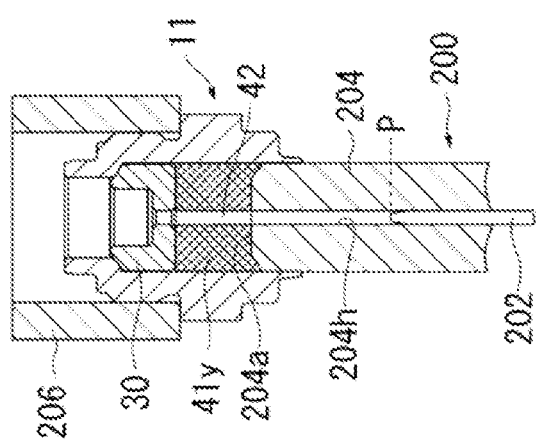

Next, as shown in FIG. 2(e), the pressing force of the pressing jig 206 is removed, and the metallic pin 202 is moved downward so as to pull out the metallic pin 202 from the first insertion hole 32 and the second insertion hole 42. Notably, the step shown in FIG. 2(e) corresponds to the "pin pulling out step" in the claims.

At that time, an axial position P to which the metallic pin 202 is pulled out (hereinafter may be referred to as the "pull-out position") is adjusted. In the present example, a portion (on the rear end 29 side) of the sensor element 21 to be inserted in the next insertion step is inserted into the center hole 204h of the tube portion 204 as well. Accordingly, the forward end of the metallic pin 202 whose pull-out position P has been adjusted within the center hole 204h comes into contact with the sensor element 21 (on the rear end 29 side). Thus, the insertion depth of the sensor element 21 in the direction of the axis O; i.e., the position at which the sensor element 21 is fixed to the metallic shell 11, can be defined by the metallic pin 202, whereby positioning of the sensor element 21 is facilitated.

Figure 2F:
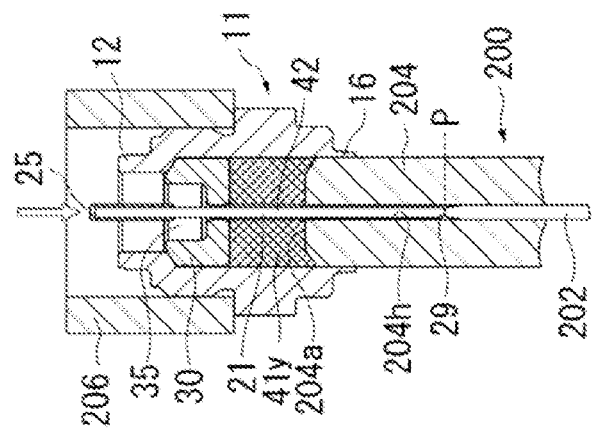

Next, as shown in FIG. 2(f), a portion of the sensor element 21 located on the rear end 29 side is inserted into the first insertion hole 32 and the second insertion hole 42 from the upper side of the metallic shell 11 (the forward end side where the cylindrical portion 12 is present). Notably, the step shown in FIG. 2(f) corresponds to the "insertion step" in the claims. In the present example, a portion of the sensor element 21 located on the forward end side is covered with the protection layer 25 which is larger in transverse cross section than the sensor element 21 itself, and the protection layer 25 cannot be inserted into the first insertion hole 32 and the second insertion hole 42. Therefore, a portion of the sensor element 21 on the rear end 29 side is inserted. However, in the case where the protection layer 25 is not provided on the sensor element 21 and the transverse cross section of the sensor element 21 has a constant size at front and rear portions thereof, the forward end portion of the sensor element 21 may be inserted from the rear end side of the metallic shell 11 (the side were the cylindrical portion for crimping 16 is present).

Figure 2G:
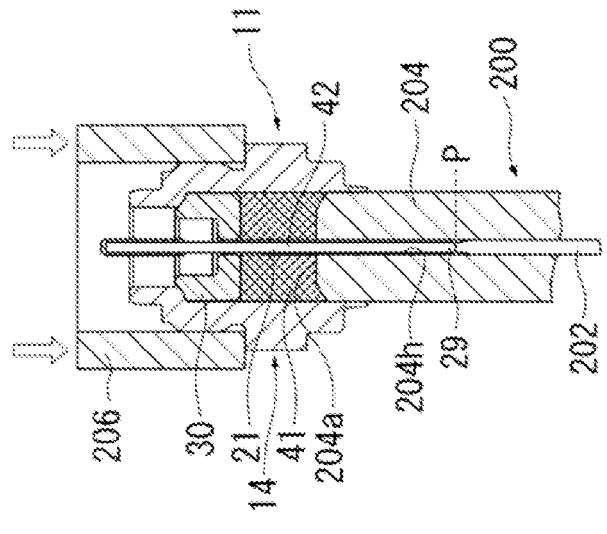

Next, as shown in FIG. 2(g), the pressing jig 206 is pressed downward (toward the jig 200). As a result, the filling member intermediate 41y is compressed by the ceramic holder 30 and the jig 200.

Since the filling member intermediate 41y formed by the above-described pre-compression step (step shown in FIG. 2(d)) is such that the powder constituting the filling member intermediate 41y is disposed approximately uniformly, occurrence of a shape-related defect can be restrained. Accordingly, when the powder constituting the filling member intermediate 41y is caused by the step shown in FIG. 2(g) to flow (relocate) around the sensor element 21 to thereby form the filling member 41, it is possible to prevent non-uniform stress from acting on the sensor element 21 through the wall surface of the second insertion hole 42, to thereby prevent breakage of the sensor element 21. Notably, the step shown in FIG. 2(g) corresponds to the "main compression step" in the claims.

Next, a gas sensor manufacturing step subsequent to the method for manufacturing a sensor intermediate product according to the embodiment of the present invention will be described with reference to FIGS. 3 and 4. FIG. 3 is a view showing a step subsequent to the steps of the method for manufacturing a sensor intermediate product according to the embodiment of the present invention. FIG. 4 is a view showing the final step of the manufacture and assembly of the gas sensor (the "assembly step" in the claims).

First, as shown on the left side of FIG. 3, the metallic shell 11 having undergone the main compression step shown in FIG. 2(g) is removed from the jig 200, is tuned upside down, and the sleeve 43 and the ring washer 45 are inserted from the side where the rear end 29 of the sensor element 21 is present. At that time, the ring washer 45 is disposed inside the cylindrical portion for crimping 16 at the rear end of the metallic shell 11 such that the ring washer 45 is located rearward of the sleeve 43.

Next, as shown on the right side of FIG. 3, the metallic shell 11 in this state is positioned and supported by a stationary jig 210. At the time of this support, the lower surface of the polygonal portion 14 of the metallic shell 11 is brought into contact with a positioning portion 210a of the upper surface of the stationary jig 210. After that, through use of a crimping die 212, the cylindrical portion for crimping 16 is compressed toward the forward end side and is bent inward. As a result, the filling member 41 is compressed further, whereby components, including the sensor element 21, the sleeve 43, etc., are fixed inside the metallic shell 11.

Subsequently, for example, as shown in FIG. 4, a forward-end-side semi-assembly 101 including the sensor element 21 is manufactured and assembled. Notably, the semi-assembly 101 shown in FIG. 4 can be manufactured by welding the protectors 51 and 61 to the metallic shell 11 after the manufacturing steps shown in FIG. 3 and attaching the gasket 19 to the metallic shell 11. Meanwhile, the remaining portion; i.e., a rear-end-side portion, is separately manufactured and assembled as a semi-assembly (product in process) 102. The two semi-assemblies are combined together whereby the gas sensor 1 is manufactured. Namely, as shown in FIG. 4, the two semi-assemblies are disposed coaxially, and a portion (near the rear end 29) of the element 21 projecting from the semi-assembly 101 located on the lower side is relatively inserted into the space between the metallic terminals 75 disposed in the metallic terminal holding member 91 to face each other. Thus, by means of spring force, the metallic terminals 75 are brought into pressure contact with the electrode terminals 24 provided on a portion of the element 21 located near the rear end 29. Subsequently, the small diameter sleeve portion 83 of the protection sleeve 81 located at the rear end thereof is crimped, and the large diameter sleeve portion 82 of the protection sleeve 81 located at the forward end thereof is fitted onto the cylindrical portion 15 of the metallic shell 11 located near the rear end thereof. The large diameter sleeve portion 82 is laser-welded to the cylindrical portion 15 over the entire circumference, whereby the gas sensor 1 shown in FIG. 1 is manufactured.

The structure and configuration of the gas sensor of the present invention may be changed freely without departing the scope of the present invention.

For example, the shapes of the ceramic holder, the compact, the filling member, the first insertion hole, and the second insertion hole, the shape of the through hole of the metallic shell, etc. are not limited to those employed in the above-described embodiment.

In the above-described embodiment, from the disposing step to the main compression step, the metallic shell is disposed on the jig such that the forward end side of the metallic shell is located on the upper side. However, the metallic shell may be disposed on the jig such that the forward end side of the metallic shell is located on the lower side.

In the above-described embodiment, the sensor element is a strip-shaped sensor element having a rectangular transverse cross section. However, the sensor element to which the present invention is applied may have a square transverse cross section or a transverse cross section of any other shape. In the above-described embodiment, the present invention is embodied for a full-range fuel air ratio gas sensor. However, the sensor manufacturing method of the present invention can be applied to other gas sensors and temperature sensors.

DESCRIPTION OF REFERENCE NUMERALS

1: gas sensor
11: metallic shell
18: through hole
18a: step portion
21: sensor element
22: detection section
25: protection layer
29: rear end of the sensor element
30: ceramic holder (holder)
32: first insertion hole
41: filling member
41x: talc ring
41y: filling member intermediate
42: second insertion hole
81: protection sleeve
202: metallic pin
204h: support hole
O: axial direction
P: axial pull-out position of the metallic pin

What is claimed is:
1. A method for manufacturing a sensor intermediate product, comprising:
   a preparation step of:
      disposing a tubular holder and a tubular compact in a tubular metallic shell, the tubular holder defining a first insertion hole, the tubular compact comprising compacted powder and defining a second insertion hole, the tubular metallic shell defining a through hole, having an inner wall surface with a circumference, and including a step portion projecting inward along the circumference of the inner wall surface, in such a manner that the tubular holder engages the step portion and the tubular compact is stacked on a side of the tubular holder opposite the step portion, and
      inserting a metallic pin into the first insertion hole of the tubular holder and the second insertion hole of the tubular compact;

a pre-compression step of compressing the tubular compact so as to form a filling member intermediate having a shape which brings the filling member intermediate into pressure contact with the inner wall surface of the tubular metallic shell and allows removal of the metallic pin from the second insertion hole;

a pin pulling out step of pulling out the metallic pin from the first insertion hole and the second insertion hole;

an insertion step of inserting a sensor element into the first insertion hole and the second insertion hole, the sensor element extending axially; and a main compression step of compressing the filling member intermediate to thereby form a filling member which fixes the sensor element inside of the tubular metallic shell.

2. The method for manufacturing a sensor intermediate product according to claim 1, wherein the sensor element has a forward end side and a rear end side, and includes:
  a detection section provided on the forward end side and adapted to detect a specific gas component contained in a gas to be detected, and
  a protection layer provided on the forward end side and covering the detection section; and in the insertion step, a portion of the sensor element located on the rear end side of the sensor element is inserted into the first insertion hole and the second insertion hole from a forward end side of the tubular metallic shell.

3. The method for manufacturing a sensor intermediate product according to claim 1, wherein the pin pulling out step further includes adjusting an axial position to which the metallic pin is pulled out such that a forward end of the metallic pin will come into contact with an end of the sensor element in the insertion step; and the insertion step further includes bringing the end of the sensor element into contact with the forward end of the metallic pin.

4. The method for manufacturing a sensor intermediate product according to claim 1, wherein the sensor element has a shape of a plate having a rectangular cross section and extending in a longitudinal direction.

5. A method for manufacturing a sensor comprising:

a preparation step of:
  disposing a tubular holder and a tubular compact in a tubular metallic shell, the tubular holder defining a first insertion hole, the tubular compact comprising compacted powder and defining a second insertion hole, the tubular metallic shell defining a through hole, having an inner wall surface with a circumference, and including a step portion projecting inward along the circumference of the inner wall surface, in such a manner that the tubular holder engages the step portion and the tubular compact is stacked on a side of the tubular holder opposite the step portion, and
  inserting a metallic pin into the first insertion hole of the tubular holder and the second insertion hole of the tubular compact;

a pre-compression step of compressing the tubular compact so as to form a filling member intermediate having a shape which brings the filling member intermediate into pressure contact with the inner wall surface of the tubular metallic shell and allows removal of the metallic pin from the second insertion hole;

a pin pulling out step of pulling out the metallic pin from the first insertion hole and the second insertion hole;

an insertion step of inserting a sensor element into the first insertion hole and the second insertion hole, the sensor element extending axially;

a main compression step of compressing the filling member intermediate to thereby form a filling member which fixes the sensor element inside of the tubular metallic shell; and an assembly step of fixing a protection sleeve to a rear end portion of the tubular metallic shell, wherein the sensor element extends in a direction of an axis and has a shape of a plate, the tubular metallic shell surrounds the sensor element in such a manner that a forward end of the sensor element projects from the tubular metallic shell, and the tubular holder and the filling member are disposed between the tubular metallic shell and the sensor element.

6. A method for manufacturing a sensor intermediate product, comprising:

disposing a tubular holder and a tubular compact in a tubular metallic shell defining a through hole, the tubular holder defining a first insertion hole, and the tubular compact defining a second insertion hole;

preparing a preliminary assembly in which a pin is inserted into the first insertion hole and the second insertion hole;

compressing the compact so as to form a filling member intermediate having a shape which brings the compact into pressure contact with an inner wall surface of the metallic shell and allows removal of the pin from the second insertion hole;

pulling out the pin from the first insertion hole and the second insertion hole, adjusting a position to which the pin is pulled out, and inserting a sensor element into the first insertion hole and the second insertion hole such that a forward end of the pin will come into contact with an end of the sensor element; and compressing the filling member intermediate to thereby fix the sensor element inside of the metallic shell.

7. A method for manufacturing a sensor intermediate product, comprising:

disposing a tubular holder and a tubular compact in a tubular metallic shell defining a through hole, the tubular holder defining a first insertion hole, and the tubular compact defining a second insertion hole;

preparing a preliminary assembly in which a pin is inserted into the first insertion hole and the second insertion hole;

compressing the compact so as to form a filling member intermediate having a shape which brings the compact into pressure contact with an inner wall surface of the metallic shell and allows removal of the pin from the second insertion hole;

pulling out the pin from the first insertion hole and the second insertion hole and inserting a sensor element into the first insertion hole and the second insertion hole such that a forward end of the pin will come into contact with an end of the sensor element; and compressing the filling member intermediate to thereby fix the sensor element inside of the metallic shell, wherein the sensor element includes a detection section provided on a forward end side and adapted to detect a specific gas component contained in a gas to be detected and the sensor element includes a protection layer covering the detection section, and the sensor element is inserted such that a rear end portion of the protection layer is disposed on a rear end side with respect to a forward end of the metallic shell.

* * * * *